US006214568B1

(12) United States Patent
Endl et al.

(10) Patent No.: US 6,214,568 B1
(45) Date of Patent: *Apr. 10, 2001

(54) MONOCLONAL ANTIBODIES OF ISOTYPE IGG WHICH BIND SPECIFICALLY TO GLUTAMATE DECARBOXYLASE, AND USES THEREOF

(75) Inventors: Josef Endl, Weilheim; Michael Brandt, Iffeldorf; Herbert Jungfer, Starnberg; Winfried Albert, Eberfing; Rosemarie Kientsch-Engel, Feldafing; Werner Scherbaum, Ulm; Wiltrud Richter, Ulm; Thomas Eiermann, Ulm, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/124,410

(22) Filed: Jul. 29, 1998

Related U.S. Application Data

(63) Continuation of application No. 08/554,796, filed on Nov. 7, 1995, now Pat. No. 5,888,813, which is a continuation of application No. 08/173,490, filed on Dec. 27, 1993, now abandoned, which is a continuation of application No. 07/835,755, filed on Feb. 13, 1992, now abandoned.

(30) Foreign Application Priority Data

Feb. 14, 1991 (DE) .................................................. 41 04 498
Sep. 7, 1991 (DE) .................................................. 41 29 849

(51) Int. Cl.[7] ........................ G01N 33/573; C07K 16/40; C12P 21/08
(52) U.S. Cl. ........................ 435/7.4; 435/7.5; 435/70.21; 436/548; 530/388.15
(58) Field of Search .................................. 435/70.21, 7.4, 435/7.5; 530/388.15; 436/548

(56) References Cited

U.S. PATENT DOCUMENTS 5,192,684 * 3/1993 Tanihara et al. ................. 435/240.27
5,888,813 * 3/1999 Endl et al. ........................... 435/338

OTHER PUBLICATIONS

Houssaint et al., Monoclonal autoantibodies from insulin–dependent diabetic patients: autoantibodies against β–cell surface or cytoplasmic antigens. Clin. exp. Immunol. 82:44–51, 1990.*
Richter et al., Isolation of IgG Islet Cell Autoantibody–Producing B Lymphocytes from the Peripheral Blood of Type I Diabetic Patients and an ICA–Positive Non–Diabetic Individual. Horm. metabol. Res. 21:686–688, 1989.*
Baekkeskov et al., Identification of the 64K autoantigen in insulin–dependent diabetes as the GABA–synthesizing enzyme glutamic acid decarboxylase. Nature 347:151–157, 1990.*

* cited by examiner

Primary Examiner—Donna C. Wortman
(74) Attorney, Agent, or Firm—Fulbright & Jaworski, LLP

(57) ABSTRACT

The invention concerns human monoclonal antibodies of the IgG isotype against human pancreatic islet cells which can be obtained by immortalizing human lymphocytes of prediabetics or diabetics, treating the culture supernatant of the immortalized cells with a conjugate of antibodies against human Fc γ and a label, subsequently treating with human immunoglobulin, incubating with immobilized human pancreatic islet cells identifying an immortalized human cell culture which produces an antibody against pancreatic islet cells via determination of the label bound to the immobilized islet cells, isolating a human immortalized cell which produces this antibody, propagating this immortalized cell and isolating the monoclonal antibody produced by these cells. The invention also concerns a process for the isolation of an islet cell antigen to which such antibodies bind as well as a method for the determination of antibodies against an islet cell antigen of the pancreas.

8 Claims, No Drawings

MONOCLONAL ANTIBODIES OF ISOTYPE IGG WHICH BIND SPECIFICALLY TO GLUTAMATE DECARBOXYLASE, AND USES THEREOF

RELATED APPLICATION

This application is a continuation of application Ser. No. 08/554,796, filed Nov. 7, 1995 now U.S. Pat. No. 5,888,813, which is a continuation of Ser. No. 08/173,490 filed Dec. 27, 1993, abandoned, which is a continuation of Ser. No. 07/835,755, filed Feb. 13, 1992, now abandoned.

The invention concerns human monoclonal antibodies which react with islet cells of the pancreas, their use as a standard in the determination of antibodies against an islet cell antigen, as well as a method for the determination of antibodies against an islet cell antigen of the pancreas.

One often finds antibodies in the sera of prediabetics or of newly diagnosed diabetics which react with the endocrine cells of the pancreas, namely the islet cells. These antibodies are usually denoted islet cell antibodies (ICA). The typical ICAs are of the IgG isotype (G. Botazzo et al., Lancet 2 (1974) 1279–1283). They react selectively with the endocrine cells of the pancreas but not with the exocrine cells, the excretory ducts or the connective tissue. In contrast the autoreactive antibodies of the IgM isotype which can also be detected do not show a preferential staining of the islet cells, but also react in the same manner with other tissues such as the pituitary gland, thyroid gland, T-lymphocytes and adrenal gland (E. Garzelli et al., J. Clin. Invest. 77, 1986, 1627–1631; S. Srikanta et al., Mol. Biol. Med. 3, 1986, 113–127). These are probably types of natural autoantibodies of low specificity and low affinity which are also present in the blood of healthy persons (Seigneurin et al., Blood 71 (1988), 581). In contrast the presence of ICAs of the IgG isotype in serum is a predictive marker for the so-called insulin-dependent diabetes (synonymous with juvenile diabetes or type I diabetes). These autoantibodies can be detected in the serum up to nine years before the onset of diabetes.

The production of human monoclonal antibodies which are reactive against islet cells has already been attempted several times. In this connection G. Eisenbarth et al. (Nature 300, 1982, 264–267) obtained a monoclonal antibody which, however, is of the IgM isotype. E. Garzelli et al. (J. Clin. Invest. 77, 1986, 1627–1631) obtained antibodies of the IgM isotype which in addition to reacting with pancreatic tissue also reacted with the thyroid gland, peripheral nerves, the oesophagus and T-lymphocytes. S. Spitalnik et al. (International Research Symposium "The Immunology of Diabetes", American Diabetes Association Woods Hole, MA, Oct. 27–30, 1987, Abstr. 113) also obtained a polyreactive antibody of the IgM isotype. W. Richter et al. (Horm. Metabol. Res. 21, 1989, 686–688) succeeded in immortalizing the lymphocytes which produce IgG against islet cells but did not succeed in cloning these B-lymphocytes on a single cell basis. E. Houssaint et al. (Clin. exp. Immunol. 82 (1990), 44–51) obtained a human monoclonal IgG antibody which, however, only showed a positive reaction towards rat and hamster islet cell lines.

S. Srikanta and G. Eisenbarth (Mol. Biol. Med. 3 (1986), 113–127) described antigens of islet cells which were, however, not specific for islet cells. The antigens or epitopes of these antigens can also be detected in other endocrine tissues such as e.g. the pituitary gland, thyroid gland, parathyroid gland, thymus, adrenal gland and in melanocytes.

S. Baekkeskov et al. (Nature 347 (1990), 151–156) identified a further 64 kD islet cell antigen as glutamate decarboxylase (GAD). Apart from the islet cells of the pancreas, this antigen is also expressed at a high rate by the neurones of the CNS which secrete γ-aminobutyric acid. Patients with a rare neurological disease, the so-called "stiff-man-syndrome", develop autoantibodies against GAD. Almost all patients with the "stiff-man-syndrome" in addition have autoantibodies against islet cells of the pancreas so that the "stiffman-syndrome" is often accompanied by a type I diabetes mellitus. The functional relevance of GAD as an autoantigen in the "stiff-man-syndrome" as well as in type I diabetes mellitus was deduced from these observations.

It was therefore the object of the present invention to provide human monoclonal antibodies of the IgG isotype which react with an human islet cell antigen and to provide a method for the determination of antibodies against an islet cell antigen.

This object is achieved by human monoclonal antibodies of the IgG isotype against human pancreatic islet cells which can be obtained by immortalizing human lymphocytes of prediabetics or diabetics, treating the culture supernatant of the immortalized cells with a conjugate of antibodies against human Fc γ and a label, subsequently treating with human immunoglobulin, incubating with immobilized human pancreatic islet cells or immobilized GAD, identifying an immortalized human cell culture which produces an antibody against pancreatic islet cells via determination of the label bound to the immobilized islet cells or to the immobilized GAD, isolating a human immortalized cell which produces this antibody, propagating this immortalized cell and isolating the monoclonal antibody produced by these cells.

It surprisingly turned out that the monoclonal antibodies which can be obtained according to the present invention react specifically with purified GAD. After incubation with different tissue sections, the antibodies according to the present invention react with islet cells of the pancreas and with the cerebellum but not with several other tissues such as e.g. from the adrenal gland, stomach, intestine, pituitary gland, cerebral cortex, lung, liver or thyroid gland.

In this connection it surprisingly turned out that binding of the antibodies according to the present invention to pancreatic sections can be weakened or completely prevented by preincubation with a diabetic serum. This shows that the antibodies according to the present invention are not only found in the blood of the particular donor from whose blood they were obtained, but are found generally in diabetic sera and that these antibodies have a general relevance for type I diabetes mellitus.

The immortalization of human lymphocytes from prediabetics or diabetics is preferably carried out by transformation with Epstein-Barr virus (EBV). In addition other methods familiar to one skilled in the art (e.g. hybridoma technique) can also be used.

In order to detect immortalized cells which produce the desired antibody, a conjugate of antibodies against human Fc γ and a label is used. In this case a conjugate of Fab fragments binding human Fc γ and a label is preferred such as that which can be obtained according to the method of Ishikawa et al., J. Immunoassay 4 (1983), page 209.

Monovalent Fab or F(ab') fragments as well as divalent F(ab')$_2$ fragments can be used as the Fab fragments which bind Fc γ.

It is usual to use an enzyme, a fluorescent or chemiluminescent dye or a radioactive isotope as the label.

The conjugate of antibodies against human Fc γ and a label is first incubated with the culture supernatant of the immortalized cells, then treated with human immunoglobulin and finally incubated with immobilized human pancreatic islet cells or immobilized GAD. In this case pancreatic tissue sections are preferably used as the immobilized islet cells.

The immortalized cell line producing an antibody against pancreatic islet cells is then identified via determination of the label bound to the immobilized islet cells or to the immobilized GAD. Depending on the type of label, this determination is carried out by means of an appropriate enzymatic reaction or by measuring the fluorescence or chemiluminescence.

For the cloning, the cells whose culture supernatant shows a positive reaction are isolated. This is preferably carried out by means of a fluorescence-activated cell sorter. The cell clones isolated in this way are propagated and those cell clones which produce the antibodies against pancreatic islet cells are identified as described above. The antibody is then isolated from the culture supernatant of these cell clones according to methods familiar to one skilled in the art.

Those monoclonal antibodies which belong to the subclass IgG1 or IgG3 are preferred.

A preferred embodiment of the invention are monoclonal antibodies which are capable of binding to human pancreatic islet cells or to glutamate decarboxylase in an equivalent manner to the antibodies produced by the cell lines ECACC 90121401, ECACC 90121402, ECACC 90121403 or DSM ACC 2017.

The term "antibodies which are capable of binding in an equivalent manner" is understood to include antibodies which have a detectable epitope overlap with the defined known antibody. This epitope overlap can easily be detected using a competitive test system. For this, the extent to which an antibody competes with the known antibody for binding to a defined antigen or to a special epitope is examined, for example with the aid of an enzyme-immunoassay. The corresponding antigen is incubated for this with the known monoclonal antibody in a labelled form and an excess of the antibody under consideration. It is then easy to determine the extent to which the antibody under consideration can displace the defined antibody from its binding by immobilizing the complexes which form, separating the solid from the liquid phase and determining the bound label in one of the two phases. An epitope overlap is present when the displacement is at least 50% at a $10^5$-fold excess.

The antibodies obtainable from the cell lines ECACC 90121401, ECACC 90121402, ECACC 90121403 or DSM ACC 2017 are particularly preferred.

The invention also concerns the cell lines ECACC 90121401, ECACC 90121402, ECACC 90121403 or DSM ACC 2017.

In addition the invention concerns a method for the production of human monoclonal antibodies of the IgG isotype against human pancreatic islet cells by immortalizing human lymphocytes from prediabetics or diabetics, treating the culture supernatant of the immortalized cells with a conjugate of antibodies against human Fc γ and a label, subsequently treating with human immunoglobulin, incubating with immobilized human pancreatic islet cells or immobilized GAD, identifying an immortalized human cell culture which produces an antibody against pancreatic islet cells via determination of the label bound to the immobilized islet cells or to the immobilized GAD, isolating a human immortalized cell which produces this antibody, propagating this immortalized cell and isolating the monoclonal antibody produced by these cells.

Further monoclonal antibodies (HaE 12 and HAG+E 10) against the islet cell antigen GAD could be obtained by using this process in combination with the competitive test system described above which neither show an epitope overlap with the antibodies produced by the cell lines ECACC 90121401, ECACC 90121402 and ECACC 90121403 nor with one another and thus characterize further epitopes of the islet cell antigen GAD. Thus based on the determination of epitope overlap it is possible to distinguish at least four epitopes of the GAD islet cell antigen which are characterized by reactivity with the following monoclonal antibodies: 1) ECACC 90121403 and ECACC 90121401, 2) ECACC 90121402, 3) HaE 12 as well as 4) HAG+E 10.

Thus the invention also concerns a process for the production of monoclonal antibodies against epitopes of an islet cell antigen which are not recognized by known monoclonal antibodies against an islet cell antigen in which firstly monoclonal antibodies against an islet cell antigen are produced by the process according to the present invention, these are incubated in the presence of labelled known monoclonal antibodies against an islet antigen with immobilized islet cells, the bound label is detected and those antibodies are selected which can displace the known antibody from the binding.

The monoclonal antibodies HaE 12 and HaG+E 10 could be obtained using this process.

In addition the present invention concerns a process for the isolation of an islet cell antigen which binds to the antibodies produced by the cell lines ECACC 90121401, ECACC 90121402, ECACC 90121403 and/or DSM ACC 2017 by lysing human or animal pancreatic islet cells, pancreatic homogenates, or brain homogenates, in particular homogenates of the cerebellum, removing insoluble material, treating the solution with an immobilized monoclonal antibody obtainable from the cell lines ECACC 90121401, ECACC 90121402, ECACC 90121403 and/or DSM ACC 2017 or with an antibody which binds in an equivalent manner to human pancreatic islet cells and isolating the antigen binding to the antibodies.

The animal pancreatic islet cells, pancreatic homogenates or brain homogenates can for example be obtained from the corresponding organs of the pig, cow, rat or mouse.

The antibodies are preferably immobilized by binding to a gel material such as e.g. protein A sepharose CL-4B. The soluble fraction of the said tissues obtained after centrifugation is applied after lysis to this immunoadsorbent and non-binding material is washed out. Subsequently the binding antigen is eluted from the immunoadsorbent. The elution is preferably carried out using 0.05 mol/l diethylamine pH 11.5, 0.5% sodium deoxycholate.

The invention also concerns anti-idiotypic antibodies which are directed against antibodies which react with an islet cell antigen which are obtainable by immunizing with an antibody against an islet cell antigen according to the present invention and isolating the desired antibodies from the serum of the immunized animals by affinity chromatography. The immunization is carried out in the animals which are usually used for this purpose, such as sheep or rabbits.

The invention also preferably concerns monoclonal antiidiotypic antibodies obtainable by immunizing with an antibody against an islet cell antigen according to the present invention, immortalizing the spleen cells of the immunized animals, cloning those immortalized cells which produce antibodies that bind to antibodies against islet cells of the pancreas and isolating the antibodies produced by these clones by known methods.

In order to detect immortalized cells which produce the desired anti-idiotypic antibodies, the culture supernatant of the immortalized cells is incubated with an immobilized antibody against an islet cell antigen. For the detection of bound anti-idiotypic antibody from the culture supernatant, a conjugate of a label and antibodies against Fc γ of that animal species from which the immortalized cells were obtained is used. In this case a conjugate is preferred consisting of Fc-binding Fab fragments and a label as can be obtained according to the method of Ishikawa et al. J. Immunoassay 4 (1983), 209.

Monovalent Fab fragments or F(ab') fragments, as well as divalent F(ab')$_2$ fragments can be used as the Fc γ-binding Fab fragments.

An enzyme, a fluorescent dye or chemiluminescent dye, or a radioactive isotope is usually used as the label.

The invention also concerns a process for the production of anti-idiotypic antibodies by immunization with an antibody according to the present invention against an islet cell antigen and isolation of the anti-idiotypic antibody from the serum of the immunized animals by affinity chromatography.

Furthermore the invention preferably concerns a process for the production of monoclonal anti-idiotypic antibodies by immunizing with an antibody according to the present invention against an islet cell antigen, immortalizing the spleen cells of the immunized animals, cloning those immortalized cells which produce antibodies that bind to antibodies against islet cells of the pancreas and isolating the antibodies produced by these clones using known methods.

Finally the invention also concerns a method for the determination of antibodies against an islet cell antigen by incubating the analytical material to be examined with a first receptor which is immobilized before or during the test reaction and detecting the bound antibody present in the analytical material by means of a labelled second receptor which binds to this antibody.

The culture supernatant of antibody-producing cells, an isolated antibody or a body fluid, preferably serum from a test person, can be used as the analytical material.

The first receptor used to detect the antibodies in the analytical material can be immobilized in test tubes or on microtitre plates. In this case the complete natural GAD antigen as well as the epitope responsible for binding in the form of a fragment of this GAD antigen can be used as the first receptor.

In a preferred embodiment of the method according to the present invention for the determination of antibodies against islet cells of the pancreas an anti-idiotypic antibody which carries the internal image of the corresponding epitope is used as the immobilized first receptor.

For the immobilization, the first receptor is preferably biotinylated and subsequently bound to a solid phase coated with streptavidin.

In a further embodiment the first receptor can also be used in the form of a tissue section, preferably of pancreatic tissue, pancreatic islets or pancreatic islet cells.

The labelled islet cell antigen GAD or preferably a labelled antibody against human immunoglobulin, preferably against human Fc γ, is used as the labelled second receptor. All labelling methods familiar to one skilled in the art can be used as the label. The detection of the bound sample antibody is carried out after separating the liquid from the solid phase by determining the label in the isolated liquid or solid phase. The quantification of the antibody in the analytical material is carried out by comparing the measured value with the value obtained for a standard antibody of known concentration.

A human monoclonal antibody against human pancreatic islet cells according to the present invention is preferably used as the standard antibody. By this means it is possible to avoid interferences in the determination caused by antibodies against mouse immunoglobulins in the patient serum when for example murine antibodies are used.

The invention therefore also concerns the use of the human monoclonal antibodies according to the present invention as a standard for the determination of antibodies against an islet cell antigen in the analytical material.

Finally the invention in addition concerns a method for the determination of antibodies against an islet cell antigen by incubating the analytical material to be examined with a first receptor which is immobilized before or during the test reaction and detecting the bound antibody present in the analytical material by means of a labelled second receptor which binds to this antibody whereby the amount of antibody present in the analytical material is determined by comparison with the measured value obtained for a human monoclonal antibody according to the present invention.

The cell lines UH33/139.464 (ECACC 90121401), IID9-402 (ECACC 90121402) and AH25/43-116 (ECACC 90121403) according to the present invention were deposited on 14.12.1990 at the ECACC, Public Health Laboratory Service, Porton Down, Salisbury, Wiltshire SP 5 OJG, United Kingdom.

The cell line MAK <GAD>H-HaE 12 was deposited on 21.08.1991 at the Deutsche Sammlung von Zellkulturen und Mikroorganismen GmbH, Mascheroderweg 1 b, D-3300 Braunschweig, under the number DSM ACC 2017.

The invention is elucidated by the following examples:

EXAMPLE 1

Selection of donors for the isolation of lymphocytes

The following procedure was used to select donors which are most likely to have in vivo preactivated lymphocytes against islet cell antigens:

Blood was collected from prediabetics or newly diagnosed diabetics and serum was prepared by a known method. This serum was tested in a serial dilution on human pancreatic sections by the following method:

25 μl of the serum from the test person was diluted in a geometric series, applied to unfixed human pancreatic sections and incubated for two hours in a humid chamber at room temperature. After washing the sections 3 times for 5 minutes each time in PBS (phosphate buffered saline, according to Dulbecco and Vogt, J. Exp. Med. 99 (1954), 167–182, without $Ca^{2+}$ and $Mg^{2+}$), 25 μl of an anti-human IgG antibody (5 μg/ml) labelled with fluorescein isothiocyanate was added and incubated for 1 hour at room temperature. After washing the sections again, they were embedded with Mowiol® (Hoechst) and the islet cell staining was evaluated with the aid of a fluorescent microscope (excitation at 476 nm, detection at 530 nm).

Only those lymphocyte donors whose sera still showed a positive reaction at a dilution of 1:64 or more were used for the isolation of lymphocytes.

20–50 ml blood was collected from the corresponding donors and the mononuclear cells were isolated from this by means of a density gradient. Subsequently these cells were immortalized by Epstein-Barr virus (EBV) transformation.

For this the mononuclear cells were incubated for 2 hours at 37° C. and 5% $CO_2$ in RPMI 1640 medium (containing 10% FCS, foetal calf serum) at a cell density of $2 \times 10^6$ cells/ml with 1 ml of the culture supernatant of the B 95-8 marmoset cell line (ATCC CRL 1612) containing EBV. The cells were subsequently washed and $2 \times 10^4$ cells were seeded in each well of a 96 well microtitre plate. 0.1% phytohaemagglutinin (Gibco, USA) was added to the medium at the beginning of the culture.

EXAMPLE 2
Cloning the EBV lines

After three to four weeks the culture supernatants of the EBV lines were tested for reactivity with islet cells of the pancreas.

For this a conjugate of human Fc γ binding Fab fragments and peroxidase (25 μl, 20 U/ml) is first added to 25 μl of the culture supernatant. This conjugate was prepared according to the method of Ishikawa et al., J. Immunoassay 4 (1983) 209. After incubating for 1 hour at 37° C., half the volume of 10% normal human serum is added and it is again incubated for 1 hour at 37° C. This mixture was applied to the pancreatic sections and incubated for 2 hours at 4° C. After a washing step (3×5 minutes in PBS) and a 3 minute preincubation of the sections in 0.1 mol/l acetate buffer, pH 4.5, they were stained immunohistochemically by incubation with 0.02% aminoethylcarbazole and 0.01% $H_2O_2$ for 15–25 minutes at room temperature. They were evaluated under a light microscope. Those EBV lines whose culture supernatant showed a positive reaction (staining of the islet cells) were cloned. For this the cells were placed singly in 96 well microtitre plates with the aid of a fluorescent activated cell sorter and fed with irradiated peripheral blood lymphocytes ($5 \times 10^4$ cells/well, 4000 rad). The lymphocyte clones obtained in this way are cultured in Iscove's modified Dulbecco's complete medium (Gibco, with 15% FCS). The antibodies are isolated from the supernatant by ammonium sulphate precipitation and affinity chromatography e.g. over protein A or protein G sepharose.

EXAMPLE 3
Investigation of the cross-reactivity with different human tissues and animal pancreata.

It was investigated whether the monoclonal antibodies isolated from the cell lines react specifically with human pancreatic islet cells. For this the antibodies from the culture supernatant were first incubated with a conjugate of human Fcγ-binding Fab fragments and peroxidase as described in Example 2. The labelled antibodies were tested on a series of different human tissue sections as well as on different animal pancreatic sections. The binding to the tissues was tested by immunohistochemical staining with aminoethylcarbazole as described in Example 2. Tables I and II show the results of these tests.

TABLE I

| Human monoclonal antibodies | | | | | | |
|---|---|---|---|---|---|---|
| Human tissue | UH33 | IID9 | AH25 | HaC11 | HaE12 | HAG + E 10 |
| Pancreas | ++ | +++ | + | + | + | + |
| Adrenal gland | – | – | – | – | – | – |
| Stomach | – | – | – | – | – | – |
| Intestine | – | – | – | – | – | n.t. |
| Pituitary gland | – | – | – | – | – | – |
| Cerebral cortex | – | – | – | – | – | – |

TABLE I-continued

| Human monoclonal antibodies | | | | | | |
|---|---|---|---|---|---|---|
| Human tissue | UH33 | IID9 | AH25 | HaC11 | HaE12 | HAG + E 10 |
| Lung | – | – | – | – | – | n.t. |
| Liver | – | – | – | – | – | n.t. |
| Thyroid gland | – | – | – | – | – | – |
| Cerebellum | + | ++ | + | + | + | + | n.t. not tested

TABLE II

| | Pancreas from | | | |
|---|---|---|---|---|
| Monoclonal antibody | Pig | Cow | Rat | NOD mouse (non obese diabetic) |
| UH33 | + | + | + | + |
| IID9 | + | + | + | + |
| AH25 | + | + | + | + |
| HaC 11 | + | + | + | + |
| HaE 12 | + | + | + | + |
| HAG + E 10 | + | + | + | + |

EXAMPLE 4
Determination of the competition of antibodies according to the present invention with serum from diabetics 20 μl each of diabetic serum, serum from healthy control persons or PBS/BSA (PBS with bovine serum albumin) are diluted 1:8, applied to normal pancreatic sections and incubated for 30 min at room temperature. Afterwards they are washed twice for 10 min. with PBS. In the meantime a conjugate of peroxidase and Fab fragments from sheep which bind human Fc γ fragments (25 μl; 20 U/ml) is added to 25 μl of the human monoclonal antibodies against the islet cell antigen GAD. This conjugate is prepared according to the method of Ishikawa et al., J. Immunoassay 4 (1983), page 209. These preformed immune-complexes are applied to the normal pancreatic sections which were preincubated with the sera, incubated for 2 hours at 4° C. and washed three times for 10 min. with PBS. The peroxidase staining is carried out using aminoethylcarbazole as described in Example 2 and subsequently a light microscope was used to assess whether the staining was diminished or not by preincubation with the individual sera in comparison to preincubation with PBS/BSA.

This shows that normal sera have no influence on the subsequent binding of the monoclonal antibodies against islet cells on the section whereas the three diabetic sera inhibit the binding of the monoclonal antibodies against islet cell antigens in different ways. This indicates that there are antibodies in the diabetic sera which recognize the same epitope as the monoclonal antibodies against islet cells according to the present invention or an epitope which is very close to this. This means that the monoclonal antibodies against islet cells which have been isolated here represent antibodies which are present in several diabetic sera and that their respective epitopes correspond to autoantigens which are relevant to the disease of diabetes.

TABLE III

| Preincubation with | ICA level JDF units | Reactions of pancreatic sections | | | | | |
|---|---|---|---|---|---|---|---|
| | | AH25 | HaC11 | UH33 | HaE12 | IID9 | HAG + E10 |
| PBS/BSA | – | ++ | + | + | +++ | +++ | ++ |
| Serum of diabetic 1 | 1280 | (+) | – | – | – | – | – |
| Serum of diabetic 2 | 640 | + | + | (+) | – | + | (+) |
| Serum of diabetic 3 | 160 | + | + | – | + | (+) | + |
| Control serum 1 | – | ++ | + | ++ | +++ | +++ | ++ |
| Control serum 2 | – | ++ | + | ++ | +++ | +++ | ++ |

EXAMPLE 5
Determination of the epitope overlap of antibodies against islet cells of the pancreas A competitive enzyme-immunoassay was carried out to detect the epitope overlap of an antibody with the monoclonal antibody ECACC 90121401, ECACC 90121402, ECACC 90121403 or DSM ACC 2017.

The antibody under examination was incubated in different dilution steps for 1 hour at room temperature with human pancreatic sections and washed 3×5 min in PBS. Subsequently peroxidase-labelled immune-complexes composed of the above-mentioned monoclonal antibodies and a conjugate of human Fc γ-binding Fab fragments and peroxidase (prepared as described in Example 2) are applied to the pancreatic sections and incubated for 2 hours at 4° C. After washing again (3×5 min. in PBS), bound peroxidase-labelled antibody ECACC 90121401, ECACC 90121402, ECACC 90121403 or DSM ACC 2017 was detected by immunohistochemical staining with aminoethylcarbazole (as described in Example 2). The staining which was obtained was compared with the staining which was obtained after incubation with the monoclonal antibody ECACC 90121401, ECACC 90121402, ECACC 90121403 or DSM ACC 2017 alone.

If there is an at least 50% competition at a $10^5$-fold excess of the antibody under assessment compared to the monoclonal antibody ECACC 90121401, ECACC 90121402, ECACC 90121403 or DSM ACC 2017 then an epitope overlap is present. In this way it was possible to show that a further antibody against an islet cell antigen of the pancreas, HaC 11, recognizes an epitope which overlaps with the epitope recognized by the antibody ECACC 90121402.

EXAMPLE 6
Isolation of islet cell antigen by immunoaffinity chromatography a) Production of the immunoadsorbent Protein A—sepharose CL-4B is shaken carefully in 0.1 mol/l borate buffer pH 8.2 with the human monoclonal antibody (ECACC 90121401, ECACC 90121402, ECACC 90121403 or DSM ACC 2017; 1 ml sepharose binds 20 mg antibody) for 1 hour at room temperature. The sepharose is then washed free of protein with 0.1 mol/l borate buffer pH 8.2 and a column is filled with it. The column material is equilibrated with 0.15 mol/l NaCl; 0.01 mol/l Tris-HCl pH 8.2; 1 mmol/l EDTA; 0.5% Triton X-100.

b) Isolation of the islet cell antigen

Isolated human pancreatic islet cells obtained by limited proteolysis of pancreatic tissue and density centrifugation are lysed by treatment with 0.15 mol/l NaCl; 0.01 mol/l Tris HCl pH 8.2; 1 mmol/l EDTA; 0.5% Triton X-100; 2 mmol/l phenylmethylsulfonylfluoride for half an hour on ice. After removing the cell particles by centrifugation at 20000 g, the lysate is pumped slowly (0.2 ml/min) over the immunoadsorbent column prepared according to a). The column is subsequently washed with the following solutions in succession (10 column volumes in each case):

a): 0.5 mol/l NaCl; 0.05 mol/l Tris HCl, pH 8.2; 1 mmol/l EDTA; 0.5% Triton X-100 b): 0.15 mol/l NaCl; 0.5% sodium deoxycholate c): 0.15 mol/l NaCl; 0.01 mol/l Tris HCl pH 8.2; 1 mmol/l EDTA; 0.05% Triton X-100.

The antigen bound to the immunoadsorbent is eluted by means of 0.05 mol/l diethylamine pH 11.5, 0.5% sodium deoxycholate. An aliquot of the column eluate is bound adsorptively to a solid phase (nitrocellulose or microtitre plate) and incubated for 2 hours at room temperature with a solution of an isolated islet cell antibody (1 μg/ml) produced by the cell lines ECACC 90121401, ECACC 90121402, ECACC 90121403 or DSM ACC 2017 and subsequently washed with 3×350 μl 0.15 mol/l NaCl/0.05% Tween 20. Bound antibody is detected by incubating with 100 μl of a peroxidase-labelled sheep-antihuman Fc γ antibody (Boehringer Mannheim, Cat. No. 1 089 196, 100 mU/ml in PBS/0.5% BSA) for 1 hour at room temperature while shaking and subsequently washing three times with 350 μl 0.15 mol/l NaCl/0.05% Tween 20. Afterwards 100 μl ABTS® (1 mg/ml, Boehringer Mannheim GmbH, Cat. No. 756 407) in 40 mmol/l citrate buffer pH 4.4 containing 3.25 mmol/l sodium perborate is added and the absorbance at 405 nm is measured after a 30 minute incubation at room temperature.

The fractions which react positively are pooled, neutralized by addition of 0.5 mol/l $NaH_2PO_4$ and subsequently dialysed against 0.15 mol/l NaCl; 0.01 mol/l Tris-HCl, pH 8.2; 1 mmol/l EDTA; 0.05% Triton X-100.

EXAMPLE 7
Determination of islet cell antibodies (ICA) with the ELISA technique:

a) coating of microtitre plates or test tubes with the first receptor

The first receptor (e.g. an islet cell antigen) is biotinylated via its amino groups with D-biotinyl-ε-amido-caproic acid-N-hydroxysuccinimide ester or via tyrosine residues with diazopara-amino-benzoylbiocytin according to the instructions of the manufacturer.

Subsequently 150 μl of the biotinylated receptor (0.5 μg/ml in PBS without $Mg^{2+}$ and $Ca^{2+}$) is incubated for 30 minutes at room temperature with a streptavidin coated solid phase (microtitre plates or test tubes, prepared according to EP-A 0 344 578) and washed with 0.15 mol/l NaCl/0.05% Tween 20.

b) Incubation with the analytical material

Serum from test subjects is diluted 1:25 with PBS which contains 0.5% BSA (bovine serum albumin) and 100 μl of this dilution is pipetted onto the receptor immobilized according to a). 100 μl of an isolated islet cell antibody (1 μg/ml PBS/0.5% BSA) is used as a positive control. Subsequently they are incubated for 2 hours at room temperature while shaking and finally washed with 3×350 μl 0.15 mol/l NaCl/0.05% Tween 20.

c) Substrate reaction

For the detection of bound ICA from the analytical material, an incubation is carried out for 1 hour at room temperature while shaking with 100 μl of a peroxidase-labelled sheep antihuman-Fc antibody (Boehringer Mannheim GmbH, Cat. No. 1 089 196, 100 mU/ml in PBS/0.5% BSA) and subsequently washed 3× with 350 μl 0.15 mol/l NaCl/0.05% Tween 20. Afterwards 100 μl ABTS® (1 mg/ml, Boehringer Mannheim GmbH, Cat. No. 756 407) in 40 mmol/l citrate buffer pH 4.4, containing 3.25 mmol/l sodium perborate is added and the absorbance is measured at 405 nm after a 30 minute incubation at room temperature.

EXAMPLE 8

Determination of the reaction of human monoclonal antibodies with purified glutamate decarboxylase (GAD) from pig brain GAD was purified from pig brain according to the method of Spink et al. (J. Neurochemistry, 40, 4, (1983) 1113). For the experiments described in the following, a fraction from the sepharose S-200 gel filtration was used in which the enzyme was present in ca. 90% purity.

The enzyme was adjusted to a concentration of 10 ug/ml in coating buffer and pipetted into Nunc Maxisorp immunoplates (50 μl/well). After incubating for 1 hour at 37° C., the coating solution was removed with a pipette and the unspecific binding sites of the microtitre plate were saturated with 1% Crotein C in PBS (200 μl/well; 1 hour at 37° C.).

In the meantime a peroxidase conjugate of sheep Fab fragments which bind human Fc γ fragments (25 μl; 20 U/ml) was added to 25 μl of the culture supernatants which contained the corresponding human monoclonal antibodies. This conjugate was prepared according to the method of Ishikawa et al., J. Immunoassay 4 (1983) 209. After incubating for 1 hour at 37° C., half the volume of 10% normal human serum was added and incubated again at 37° C. for 1 hour.

This mixture was dispensed into the antigen-coated and washed wells of the microtitre plate and incubated for 2 hours at 4° C.

After a washing step (3× with PBS/0.05% Tween 20), 100 μl ABTS® (1 mg/ml in 40 mmol/l citrate buffer, pH 4.4 containing 3.25 mmol/l sodium perborate) was added and the absorbance was measured at 405 nm after a 45 minute incubation at room temperature.

Table III shows the results of the reaction of the monoclonal antibodies used with purified pig brain GAD.

| Monoclonal antibody | mA 405 nm | Antibody concentration (μg/ml) |
| --- | --- | --- |
| AH 25 (ECACC 90121403) | 694 | 2.0 |
| UH 33 (ECACC 90121401) | 458 | 3.3 |
| II D9 (ECACC 90121402) | 691 | 22.0 |
| H-IgG 1 myeloma protein (negative control) | 10 | 20.0 |

What is claimed is:

1. Human monoclonal antibody which is of isotype IgG and which binds, specifically, to glutamate decarboxylase.

2. The human monoclonal antibody of claim 1, which is of subclass IgG1.

3. The human monoclonal antibody of claim 1, which is of subclass IgG3.

4. A process for production of the human monoclonal antibody of claim 1, comprising:

(i) immortalizing a lymphocyte of a human diabetic or prediabetic;

(ii) culturing the immortalized lymphocyte to produce a supernatant;

(iii) treating said supernatant with a conjugate of anti-human Fcγ antibody and a label to form a complex between said conjugate and antibodies present in said supernatant;

(iv) treating said supernatant with human immunoglobulin;

(v) incubating said supernatant with immobilized glutamate decarboxylase so as to immobilize complexes containing antibodies which specifically bind to glutamate decarboxylase;

(vi) identifying the supernatant containing said antibody;

(vii) isolating said immortalized lymphocyte producing said supernatant;

(viii) culturing said immortalized lymphocyte under conditions favoring production of said antibody; and (ix) isolating monoclonal antibodies produced thereby.

5. The process of claim 4, further comprising contacting said monoclonal antibody with a labelled monoclonal antibody which specifically binds to immobilized glutamate decarboxylase and determining binding of said labelled monoclonal antibody to immobilized glutamate, decarboxylase or lack thereof to determine if the monoclonal antibody has specificity differing from said labelled monoclonal antibody.

6. Method of claim 4, further comprising immobilizing said complex between first receptor and antibody.

7. A method for determining an antibody which specifically binds to glutamate decarboxylase, comprising contacting a sample with an immobilized or immobilizable first receptor which specifically binds to said antibody to form a complex therebetween, contacting said complex with a second, labelled receptor which specifically binds to said antibody, determining label containing complexes, and carrying out a control assay by combining said first receptor and second, labelled receptor with a defined amount of the human monoclonal antibody which specifically binds to glutamate decarboxylase of claim 1, and determining antibody which binds to glutamate decarboxylase in said sample thereby.

8. The method of claim 7, wherein said first receptor is biotinylated.

* * * * *